(12) United States Patent
Madill et al.

(10) Patent No.: US 6,647,288 B2
(45) Date of Patent: Nov. 11, 2003

(54) METHOD AND APPARATUS FOR DESIGNING A WORKSTATION

(76) Inventors: Peter V. Madill, 7005 Hazel Cotter Ct., Sebastopol, CA (US) 95472; Ray T. Flugger, 100 Stoney Point Rd., #125 Santa Rosa, CA (US) 95401

( * ) Notice: Subject to any disclaimer, the term of this patent is extended or adjusted under 35 U.S.C. 154(b) by 216 days.

(21) Appl. No.: 09/779,885

(22) Filed: Feb. 9, 2001

(65) Prior Publication Data

US 2002/0111557 A1 Aug. 15, 2002

(51) Int. Cl.[7] .................................................. A61B 5/04
(52) U.S. Cl. .................... 600/546; 600/587; 128/898
(58) Field of Search .................... 600/300, 544–546, 600/587, 594, 595; 128/897, 898, 905, 920; 482/9; 33/511, 512; 434/72, 219, 234

(56) References Cited

U.S. PATENT DOCUMENTS

| | | | |
|---|---|---|---|
| 4,571,682 A | | 2/1986 | Silverman et al. |
| 4,683,891 A | | 8/1987 | Cornellier et al. |
| 4,807,642 A | * | 2/1989 | Brown ........................ 600/546 |
| 4,912,638 A | | 3/1990 | Pratt, Jr. |
| 5,085,226 A | | 2/1992 | DeLuca et al. |
| 5,163,440 A | | 11/1992 | DeLuca et al. |
| 5,490,517 A | * | 2/1996 | Whitman et al. ........... 600/587 |
| 5,645,073 A | * | 7/1997 | Kadefors et al. ........... 600/546 |
| 5,792,047 A | | 8/1998 | Coggins |
| 5,795,310 A | * | 8/1998 | Berlin ........................ 600/595 |
| 5,964,719 A | * | 10/1999 | Costello et al. ............. 600/595 |

OTHER PUBLICATIONS

Ray et al.; "Ergonomics Evaluation of Working Posture Adopted by Women Engaged in Small Scale Industries," Proceedings of the First Regional Conference, IEEE (1995), Abstract.*

Melin; "Occupational Physiotherapy in a Large Industry," Ergonomics: The Physiotherapist in the Workplace, 1990, abstract.*

* cited by examiner

Primary Examiner—Charles A. Marmor, II
(74) Attorney, Agent, or Firm—Dorsey & Whitney LLP (57) ABSTRACT

An electrophysiological monitoring apparatus for designing a workstation (21, 21p). The monitoring apparatus preferably is a surface electromyography apparatus which includes pairs of electromyography electrodes sensors (31a, 31b; 32a, 32b; 33a, 33b) with appropriate grounding formed for attachment to a worker (24), a signal processor (37) connected to the electrodes and formed to process output signals from the electrodes and produce muscle loading profiles (101, 111, 121, 131) therefrom. The apparatus further includes a workstation (21, 21p) having an adjustable physical geometry capable of variation so as to change the manner of movement of the worker's muscles during performance of the task. The apparatus (21, 37) is used in a method to select a workstation configuration most desirable for extended use by the worker. The optimized overall workstation (21p) may be customized and used to train an individual worker (24) to lower his or her muscle loading profiles during performance of the task.

24 Claims, 3 Drawing Sheets

METHOD AND APPARATUS FOR DESIGNING A WORKSTATION

TECHNICAL FIELD

The present invention relates, in general, to the use of electrophysiological monitoring devices, such as surface electromyography apparatus, to sense muscle loading, and more particularly, relates to the ergonomic design of the human operator interface of workstations at which workers perform repetitive tasks using such apparatus.

BACKGROUND ART

Repetitive tasks, for example, those performed in industrial or manufacturing settings at workstations, frequently cause worker injuries which are serious enough to result in the need for the worker to take sick leave and undergo physical and other medical and manipulative therapies in order to attempt to rehabilitate damage caused by chronic muscle overloading or fatigue. Neck, pectoral girdle, upper extremity, forearm, hand and back injuries regularly occur, with the result that the worker must seek medical assistance and the employer is faced with considerable worker downtime. Some professionals in the field worry that there is an epidemic of upper extremity work related repetitive motion disorders.

As part of the physical therapy for injured workers, physicians and allied health professionals may employ surface electromyography apparatus, including the affixation of sensing electrodes to the injured muscles and connective tissue so as to assist in the measurement of resting and active muscle tone. It has been discovered that excessive muscle tone, especially when performing repetitive tasks at manufacturing workstations, results in excessive levels of muscle loading, that in turn result in increased vulnerability to repetitive motion injuries. Such injuries almost exclusively occur in the cervical, pectoral girdle and upper extremity muscles, ligaments, tendons and connective tissue. Thus, a number of authorities are now calling these injuries, in deference to a lack of clear understanding regarding the etiology of these disorders, "work related upper extremity disorders."

The electrical input from the muscles to the surface electromyography unit, obtained via the sensing electrodes, allows one to visually observe the degree of both resting muscle tone and muscle loading when performing repetitive tasks. The muscles being measured by such apparatus are those that are determined by prior physical examination and ergonomic analysis to be most critically involved in the repetitive motion tasks the worker is performing at his workstation. The visual feedback offered by such measuring apparatus also enables the worker to observe the relationship between muscle tone and loading and his particular industrial injury and resultant pain syndrome. Recent research is validating that the retraining offered by this electromyographic "biofeedback", in terms of its ability to promote and facilitate the workers learning of the voluntary ability to reduce muscle tone and task specific muscle loading, offers a pathway to the rehabilitation of the injured worker that results in improved recovery rates over and above that afforded by traditional physical and manipulative rehabilitative therapies.

The economic loss resulting from on-the-job injuries is more than the mere loss of man hours in that there is an associated reduction in worker morale that, in turn, reduces worker productivity. While electromyographic biofeedback therapy after an injury can reduce the number of further injuries to some degree, the repetitive nature of the tasks and the fact that nothing has really changed physically at the workstation, usually creates a high likelihood of the injury reoccurring.

The reoccurrence of such injuries and the associated psychological depression that accompanies them also can result in high worker turnover. Thus employers also are faced with reoccurring training costs, worker inefficiency and continuing poor worker morale.

One important approach to these problems is the ongoing effort on the part of industry to promote better ergonomic design of the human operator interface of manufacturing workstations. To this end, fixtures and jigs are provided which position workpieces in positions which are believed will allow the worker to perform the task with less muscle strain and stress, as well as enhance performance. Rests and tool support devices are also provided toward the end of reducing muscle fatigue.

The flow of workpieces through the workstation also will be designed to reduce worker manipulation of workpieces.

Such ergonomic designs, however, have largely been based on intuition, common sense and anecdotal experience, rather than any attempt to quantify the effects of workstation design on worker muscle loading. While current ergonomic workstation designs are a step forward, as compared to indifference, they still have geometries and configurations which can unduly stress the worker.

Accordingly, it is an object of the present invention to go beyond the use of intuitive ergonomic design techniques and to employ electrophysiological monitoring devices, such as surface electromyography apparatus, to assist in better, more appropriately informed ergonomic design of workstations to maximize the efficiency of muscle loading and thus reduce the potential for fatigue and stress and thereby contribute to the reduction and prevention of worker injury vulnerability.

Another object of the present invention is to provide a biofeedback method and apparatus for designing the human operator interface of manufacturing workstations at which repetitive tasks can be performed that are ergonomically enhanced and produce reduced muscle loading during performance of tasks at the workstation.

Still another object of the present invention is to customize an already electrophysiologically designed workstation to better adopt the human operator interface to the bodily dimensions of the individual worker so that the individual worker can adjust the interface to his or her particular physical stature.

Still a further object of the present invention is to provide an apparatus and method for designing a workstation which can accommodate workers of a widely varying physical stature, is adaptable to a wide range of different types of workstations and repetitive tasks, can be employed in rehabilitative situations, can be used as a screening test to avoid misplacement of workers and is capable of achieving substantial economic savings for the employer, as well as enhancing worker morale and physical well-being.

The apparatus and method of the present invention has other objects and features of advantage which will be described in more detail in the following Best Mode Of Carrying Out The Invention or will be apparent from the accompanying drawings.

SUMMARY OF THE INVENTION

The method of designing a workstation of the present invention is comprised, briefly, of the steps of determining a plurality of muscle loading profiles for the muscles of a worker using biofeedback or electrophysiological monitoring apparatus, such as surface electromyography apparatus, while the worker is performing a task at a workstation for a plurality of different worker/workstation relative positions; and selecting a worker/workstation relative position for extended use by the worker based upon the one of the plurality of relative positions producing substantially the lowest muscle loading profile for the worker during the determining step. In the preferred method the determining step is accomplished by varying the physical geometry in terms of the location of critical operating fixtures at the workstation so as to change the relative position between the worker and the workstation during performance of the task at the workstation. The determining step further is preferable accomplished by securing a plurality of electrical muscle load sensors (electrode pairs) to monitor muscle activity of the work when performing the task at the workstation and monitoring the muscle load sensors to generate the muscle loading profiles.

The apparatus for designing a workstation for use in the performance of a task of the present invention is comprised, briefly, of at least one electrical biofeedback sensor formed for attachment to a worker for sensing muscle loading of a muscle of the worker. The most preferred sensor embodiment employs two spaced apart electrodes attached to an individual muscle along with a grounding electrode, which are responsive to sense micro-voltages produced by the worker's muscle during loading to produce a sensor output signal. A signal processor is electrically connected to the sensor and formed to process output signals from the sensor to produce a muscle loading profile during performance of the task by the worker. Finally, a workstation having an adjustable physical geometry capable of variation of the manner of movement of the worker's muscles during performance of the task. In the preferred apparatus the signal processor includes appropriate programs that perform data analysis, a storage device, and a display device electrically coupled together, with the storage device being formed for storage or a plurality of muscle loading profiles therein and the display device being formed for display of at least one muscle loading profile thereon.

In the present method a test worker, and most preferably a plurality of test workers, are selected to perform the task. The test workers may have short, medium and tall physical statures to cover a range of statures for production workers who will use the workstation. Moreover, the present method further includes the step of customizing the workstation geometry further by using electrophysiological monitoring apparatus and the specific workers who will use the workstation under production conditions.

BEST MODE OF CARRYING OUT THE INVENTION

Figure 1:
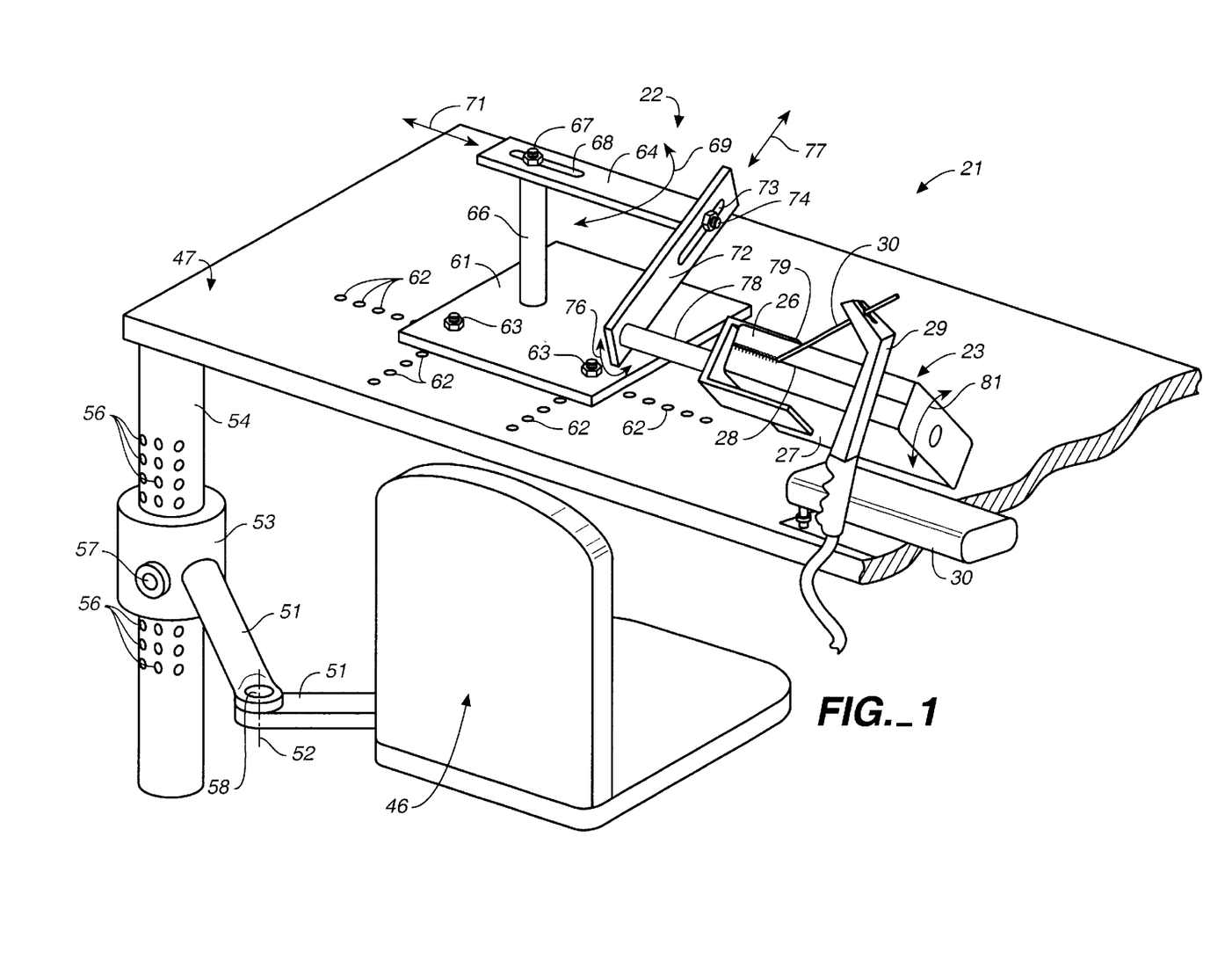
FIG. 1 is a fragmentary, top perspective view of a schematic representation of a test workstation constructed in accordance with the present invention.
Figure 2:
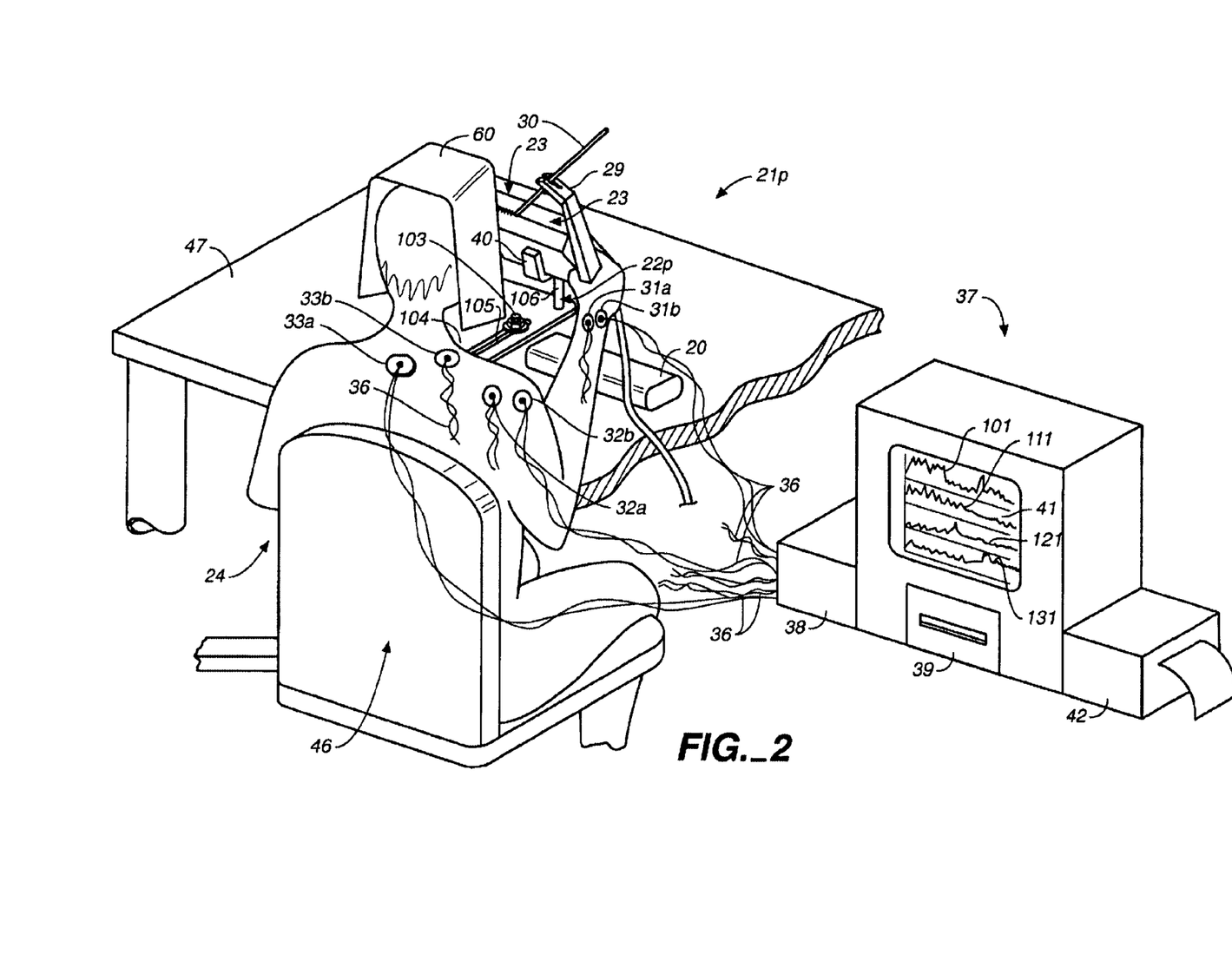
FIG. 2 is a fragmentary, top perspective view of a production workstation constructed in accordance with the present invention with a worker performing a welding task while being monitored by surface electromyography monitoring apparatus.

The present invention employs an apparatus and method for designing a workstation for the performance of tasks by a worker using electrophysiological monitoring techniques and particularly, surface electromyographic techniques. Most usually the tasks are repetitive in nature and typically employed in an industrial setting for the production, assembly or packaging of goods. A typical application for the apparatus and method of the present invention is shown in FIGS. 1 and 2 of the drawing in which a test workstation, generally designated 21, and a production workstation, generally designated 21p, include an operator interface assembly, such as fixture assemblies 22 and 22p, which hold a workpiece, in this case a muffler casing 23. The worker 24, shown in FIG. 2, is welding casing halves 26 and 27 together along a seam 28 using welding apparatus 29.

While the following description is based upon an industrial application of the present invention, it will be understood that the method and apparatus of the present invention can be readily applied to non-industrial applications involving repetitive tasks, such as, agricultural produce handling, secretarial workstation tasks, medical procedures, a wide variety of assembly line jobs, and virtually any task or job involving repetitive manual dexterity at a workstation or area at which the task is to be performed. It will also be understood that the expression "task," as used herein, also may include portions of a procedure.

Thus, when considering the overall manufacture of muffler 23, it will be realized that the worker at workstation 21 only performs one of numerous tasks which must be accomplished in the formation of the muffler. Moreover, the task performed at the workstation can include several sub-tasks, such as assembling muffler casing halves 26 and 27 together as a unit, mounting them in fixture assembly 22, 22p, welding along seam 28, removing the welded muffler from the fixture and turning it over, remounting the muffler in fixture 22, 22p, welding the opposite side, and removing the welded muffler from the fixture to place it on a conveyor or the like for transport to the next workstation. Each one of these sub-tasks can be considered a "task" within the meaning of the present invention that will be a candidate which can benefit from the present workstation design apparatus and method.

The workstation designing apparatus of present invention includes at least one electrophysiological monitoring transducer, electrode or sensor. The preferred electrophysiological monitoring apparatus is a surface electromyography apparatus in which pairs of electrodes 31a, 31b; 32a, 32b; and 33a, 33b (FIG. 2), together with a ground electrode (not shown), form a "sensor" as used herein. The electrode pairs are formed for attachment to worker 24 at positions enabling sensing of the loading of muscles of the worker. Thus, two electrodes are attached to each indicated muscle of the worker, and a ground is provided. Such surface electromyography electrodes are well known in the industry and are responsive to micro-voltage fluctuations produced by a person's muscles during rest and motion or the performance of work. Micro-voltage fluctuations can be correlated to and are indicative of muscle tone and loading during the performance of muscle contractions and relaxations. Electrodes 31a, 31b; 32a, 32b; and 33a, 33b are electrically coupled by conductors 36 to a signal processor, generally designated 37, so that output signals from sensors can be communicated to signal processor 37.

Signal processors suitable for use in the present invention are made by several long-standing medical device manufacturers in the electromyography biofeedback industry, and are licensed by the FDA for such purposes as assessment and therapy. Signal processor 37 typically will include a sensor interface 38, a storage device 39, a video display device 41, an associated output device such as a printer 42, all of which are schematically shown in FIG. 2. The signal processor will be hardwired or include software suitable for processing output signals from the sensors to produce, store, display and output muscle loading profiles (loading vs. time curves)

The final element in the apparatus of the present invention is a workstation, either test workstation 21 or production workstation 21p, having an adjustable physical geometry capable of variation of the manner of movement of the worker's muscles during performance of the task. As above noted, workstation 21 of FIG. 1 is a test workstation at which a basic or generally optimum physical geometry for the task to be performed at the workstation is established, and workstation 21p is a production workstation at which the basic workstation design is further customized to the particular or specific individuals who will be performing the task under production conditions.

Referring now to FIG. 1, the details of construction of test workstation 21 can be described. In FIG. 1 the worker and associated electromyography biofeedback apparatus are not shown in order to more clearly illustrate the construction of test workstation 21.

In the method of the present invention, workers of representative stature are to perform a task at test workstation 21. The test workstation will be similar in its overall ergonomic design to that which a designer would normally employ using intuitive or anecdotal ergonomic design criteria in order to attempt to make the worker comfortable while repetitively performing the desired task. In this case, workstation 21 includes a seat assembly 46 which is positioned before a table 47 supporting fixture assembly 22 for the workpiece 23 upon which the task will be performed.

Rather than merely relying on common sense or intuitive ergonomic design, the apparatus and method of the present invention employ surface electromyography apparatus to measure or sense worker muscle loading while performing the task at the workstation. Moreover, such measurement or sensing is undertaken for a plurality of different representative worker/workstation relative positions. Stated alternatively, test workstation 21 has an adjustable physical geometry capable of variation in a manner causing variation in the movement of the worker's muscles during performance of the task.

If, for example, the worker sits very close to workpiece 23 on seat assembly 46, his arm will be bent more at the elbow during welding, while if the workers sits farther away, his arm will be more extended. The height of the workpiece above the table will also affect the height of the worker's hand during performance of the task. The angle of the workpiece with respect to the worker will cause the worker to rotate or move his arm through a different range of movements or arcs as the task is performed. In FIGS. 1 and 2, for example, the welding proceeds from left to right. If fixture assembly 22 is adjusted, however, it could also proceed from top to bottom or bottom to top, or at an angle therebetween accommodating a right-handed or a left-handed worker.

By way of a partial illustration of the adjustable physical geometry which can be provided at a test workstation, illustrated workstation 21 includes a seat-supporting arm assembly 51 which is capable of rotation about axis 52 and is mounted by a collar 53 to a table leg 54. The table leg has a plurality of openings 56 which can receive a locking pin 57 on collar 53 so as to fix seat assembly 46 at any one of a plurality of vertically and angularly adjusted positions along leg 54. When combined with rotation about axis 52 and locking by assembly 58, the positioning of seat assembly 46 relative to table 47 can be varied substantially.

Fixture assembly 22 similarly is adjustable so as to enable a wide range of test positions to be achieved for performance of the task. Base plate 61 of fixture assembly 22 can be bolted through openings 62 by bolts 63 in a variety of locations on tabletop 47. This, of course, can be combined with the position of seat assembly 46. In addition, arm 64 can be mounted to post 66 by a bolt and washer assembly 67 which passes through a slot 68 so as to allow both angular adjustment, as indicated by arrows 69, and horizontal adjustable, as indicated by arrows 71. Transverse fixture arm 72 also may be slotted at 73 and secured by nut and washer assembly 74 for both angular adjustment, as indicated by arrows 76, and transverse adjustment, as indicated by arrows 77 Finally, post assembly 78 may be rotatable about its longitudinal axis so that clamping assembly 79 can be fixed in various angular positions, as indicated by arrows 81

Various combinations of fixture adjustments can be provided so that the position of muffler or workpiece 23 can be adjusted to virtually any orientation for the worker. Moreover, workstations 21 can include adjustable tool or worker support structures, such as armrest 30. Together the workstation includes a physical geometry which can be varied to adjust the worker's position relative to the workpiece, the position of the workpiece, the support of the worker or his or her limbs, or the support of tools used by the worker.

It is preferable in the present invention that the workers who are used to aid in the design of the basic or generally optimal workstation geometry be workers of representative stature, generally small, medium and tall, from the workforce who will be performing the production tasks. However, in some applications, for example, an employer will know that most of the workers will be female of relatively smaller stature, and appropriate test subjects representing the range of statures amongst these workers will be chosen for testing of the proposed workstation. Generally, testing is begun with a test worker whose stature is about at the median of the range of statures for production workers. This selection allows many of the initial design questions and challenges to be solved. Further refinements are made when subsequent testing includes test workers of smaller and larger stature.

Referring now to FIGS. 1 and 2, the method of assisting in the optimal ergonomic design of the human operator interface of workstations of the present invention can be described in more detail. While worker 24 and the various biofeedback apparatus shown in FIG. 2 are positioned in front of a production workstation 21p, worker 24 and the surface electromyography apparatus will be understood as also being used in connection with the test workstation 21 of FIG. 1.

As above noted, the workstation 21 will be of a general configuration which one skilled in the art of general ergonomics would employ, for example, a worker sitting before a table to perform this task, rather than standing or in some other position. Thus, the test workstation 21 can be set up with seat assembly 46 and fixture assembly 22 in a position which results in muffler 23 being positioned in front of the worker at a location which intuitively would seem likely to make performance of the task by the worker the least stressful and/or fatiguing. Such intuitive positioning of the workpiece and the worker, however, has been found, using the method of the present invention to not necessarily result in the optimal ergonomic configuration for minimization of worker muscle fatigue and facilitation of productivity. No matter how carefully the design engineer applies known and existing ergonomic principles, there remains considerable guess work and margin for error in the final placement of the various fixtures that compromise the eventual workstation setup.

A worker of average stature is positioned on seat assembly 46 in front of table 47. The workstation designer or ergonomic technician will then attach a set of paired electrodes, along with a ground electrode, to the worker at muscle groups which in the judgment of the technician or designer are likely to be the muscle groups which will undergo the most stress from the repetitive task. As shown in the drawing, electromyography sensors 31a, 31b; 32a, 32b; and 33a, 33b are attached, respectively, at the forearm extensor carpi radialis, the upper arm deltoid muscle, and the trapezius of the worker. Additionally, a pair of electrodes (not shown) might be attached to the pectoral girdle muscles infraspinatus. This attachment is accomplished in a manner well known in the industry, usually by taping (not shown) the sensor pad which has been smeared with an electrically conductive coupling gel to the worker in positions on the skin overlying the motor end plate of the muscle to be studied.

Next, the worker can pick up welding tool 29 and hold welding rod 30 in a position at the start of seam 28. When welding is to be simulated, at least in early testing, the arc welding machine would not be turned "on" and the welding rod 30 would merely be positioned at the beginning of the seam. The worker would then move the welding rod along the seam at a pace which would be typical for actual welding until the entire seam 28 has been "welded" and the task completed.

Figure 3:
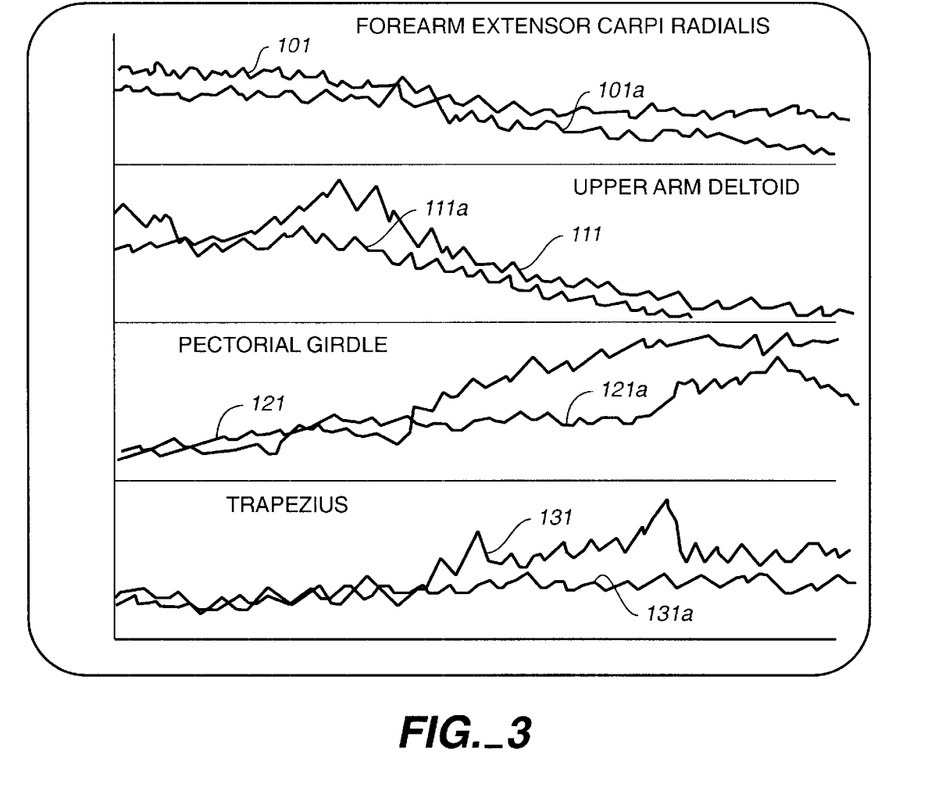
FIG. 3 are graphical schematic representations of typical muscle loading profile curves generated using the apparatus of FIGS. 1 and 2.

During the simulated welding by the worker, muscle loading at the locations of sensors or electrode pairs is input to processor 37, stored and usually simultaneously displayed to produce a plurality of muscle loading profiles 101, 111, 121 and 131. Essentially each profile is the magnitude of muscle loading as a function of time over the length of task or task segment being performed. Schematic read outs from muscle measurement profiles are shown in FIG. 3.

Usually, one of the paired electrodes will yield an electromyographic profile which varies substantially, or has a magnitude which is high, as compared to the loading profiles of the other muscles which are being monitored. This tends to identify the muscle or muscle group profile as being the most likely to be the critical muscle or muscle group (e.g., profile 111 or 121) and that which is most likely to fatigue or be overloaded by repetitive use. Based upon even one performance of the task, the technician may want to reposition one or more of the paired sensors, for example, move trapezius sensors 33a, 33b to one of the muscles mobilizing the worker's elbow so that further data are obtained from muscles which appear to be relatively active.

Having obtained at least one set of data for the initial operator interface configuration, the equipment designer and/or ergonomic engineer can now begin to reposition critical components of the workstation operator interface to change the relative position between the worker and the elements of the workstation that interact with the worker. Repeated measurements indicating loading are then made for the relevant muscles being monitored. For example, seat assembly 46 can be rotated about leg 54 in an outward or inward direction to determine the effect of the worker's body position on muscle stress. As the seat moves away from the table, the worker's arm extends which changes the range of motion of the worker's arm muscles during welding. At each changed configuration, the worker again performs a simulated weld of seam 28 and the resulting muscle loading profiles, for example, profiles 101a, 111a, 121a and 131a, are observed, stored in storage device 39 and displayed. The changes also can include simple reversing of the direction of the simulated weld.

After a plurality of seat assembly positions are tested, the workstation designer can compare the resulting muscle profiles visually or by comparison of hand written records of the different measurements obtained during the simulated work task movements made by the worker/operator. The computer based signal translation and display unit, and its associated printer, also can be employed to print out records of the muscle measurements made during the different worker interfaces tested. These printouts can subsequently be compared mentally, visually and even with analytical comparative computer programs to provide a permanent record of the testing and ergonomic design procedure. The comparisons made in this fashion look for a muscle loading profile for the most critical muscle groups that is the most desirable, usually, one having an average muscle loading profile that is substantially the lowest. As will be appreciated, some muscle loading profiles may increase as a result of changes in the relative worker/workstation position, while other loading profiles will decrease. If the forearm muscle group is generally regarded as being the most critical, the technician may select a seat position at which the forearm loading profile is lowest on average, notwithstanding that the trapezius loading profile has increased somewhat. If clinically forearm injury is the most common problem for welders, that muscle group will be minimized.

The technician can then proceed to change other elements of the worker or operator interface configuration, for example, fixture assembly 22 and support or armrest assembly 20. At the various changed configurations, the worker again simulates the workstation specific welding routines and the muscle loading profiles are measured, compared and preferably stored. The angle of muffler 23 can be varied and the height of the armrest 20 varied. These changes may produce unexpected muscle loading profiles, which in turn, may suggest the possibility of changing the seat assembly position, or transversely adjusting the fixture, or both.

Thus, the applied electromyography technician or workstation design engineer or ergonomic officer can use trial and error techniques guided by the resultant muscle loading profiles, to obtain a minimal or generally optimum combination of muscle loading profiles of various muscle groups involved in performance of the repetitive task. The approach shown in FIGS. 1 and 2 is to use an armrest 20 which can support the arm and/or wrist of the worker during welding of the seam, but it would also be possible to provide a mechanism for moving the muffler casing with the worker's left hand, while the right arm, which carries the arc welding assembly, is held steady on armrest 20. Thus, test workstation 21 also can include fixtures for movement of the workpiece, as opposed to the stationary workpiece which is illustrated in the drawing. Such movement might be controlled by the worker's other arm and therefore sensing of the muscle loading of the other arm also would be desirable.

Once the applied electromyography guided optimized operator interface configuration for workers of different stature has been determined for test workstation 21, a production workstation 21p can be constructed which has the relatively optimal physical geometry as determined at the test workstation. It is a feature of the present invention, however, that the present method includes the further step of customizing production workstation 21p to the particular worker or individual who will actually use workstation 21p. Workstation 21p will have a greatly simplified workpiece fixture 22p which can take the form of a cradle, clamping device or other fixture that will position muffler 23 at the position found to be optimal when using test workstation 21. Production fixture 22p includes some ability to make adjustments to accommodate stature differences in the particular or individual worker who will use the production workstation. Thus, a slot 105 and nut 103 can be used to secure cradle base plate 104 and cradle 40 to table 47 in various positions. Similarly the armrest 30 can be vertically adjustable, as can the cradle support post 106. The range through which all of these adjustable fixtures can operate is determined by the electromyographic testing.

Further, during the testing at test workstation 21 one of the parameters which preferably is identified is which geometry adjustments affect muscle loading profiles the most so that production workstation 21p need only have one or two adjustments to enable customization. The production worker will be seated on seat assembly 46 and again sensors will be attached, although in this case probably only one or two sensors will be needed since the critical muscle groups also would have already been identified at test workstation 21. The individual or specific production worker will then perform a simulated task, and workstation 21p will be customized by limited adjustment of fixture 22p to better accommodate the actual stature of the individual who will use the workstation. Once the muscle loading profile has been substantially optimized for the individual production worker during a simulated welding task, the production worker can actually perform the task by welding muffler casings at workstation 21p. This actual performance of the task can then be compared to previous simulated performances. Obviously, such actual welding also can take place at test workstation 21 as a final check of the optimization of the relative worker/workstation position.

The above analysis can similarly be conducted for any number of other sub-tasks to be performed at a whole variety of production workstations so as to try to minimize or reach an optimum muscle loading profile for the other tasks. Obviously, judgment and tradeoffs may be required when a plurality of tasks or sub-tasks are to be performed at the same workstation. The workstation designer or customizer may well, for example, find that a more optimal set of muscle loading profiles for a plurality of sub-tasks is achieved when none of the plurality of sub-tasks includes high peaks. Thus, a set of muscle loading profiles which have a slightly higher average loading may be desirable over a set of muscle loading profiles in which very high stress or muscle loading occurs as a result of the workstation geometry, even though the average muscle loading profile is lower. While subjective decisions are made using the apparatus and method of the present invention, sensing of muscle loading allows a very high degree of objectivity to be used to guide workstation ergonomic design.

As will be appreciated, the customizing step provides additional advantages in the process of the present invention, but it is not an absolute requirement since the basic overall design which is achieved at test workstation 21 results in substantial advantages even if each workstation is not customized to the individual worker.

Both the original workstation design and the customizing of that design to individual workers require significant investments of time and effort. The resulting workstation, however, makes up for that time and effort in terms of contributing to the prevention of work related upper extremity disorders and low back pain syndromes and in terms of enhancing worker morale and productivity. Since the workstation design resulting from the use of electrophysiological monitoring techniques reduces muscle stress, the worker feels better while performing the job and is more likely to remain on the job and have an enhanced productivity at the workstation than when performing the tasks at conventional workstations. Workstations designed with the assistance of surface electromyography reduce workers compensation claims and the worker realizes that the employer is being active and aggressive with respect to worker health issues.

Using the electrophysiological monitoring workstation design techniques of the present invention, the employer can also screen production workers so that they are not inadvertently placed at a workstation to do a physical task which will be particularly stressful or fatiguing for them. Thus, while the workstation 21p may be optimized for a worker of average stature, and even customized to accommodate stature variations and individual peculiarities, some workers still will not be able to perform the requisite task at the optimized profiles can be printed out through printer 42 and kept in the worker's personnel file. Periodically, the worker can be tested at the workstation to determine whether or not muscle loading profiles are changing over time.

An additional advantage of the apparatus and method of the present invention is that once optimization and customization are completed, the worker can be trained by medical personnel using classic biofeedback technique. The worker is directly and audiographically fed back the muscle loading information as the task is performed in an operant conditioning paradigm, rather than merely making it available to a medical technician or workstation design engineer for adjustment of the various workstation geometry parameters. Thus, the worker can learn by watching the muscle loading profiles developed while performing a task how to further maximize the efficiency of performing this task and thus to streamline and minimize the effort required to perform the task.

Obviously, some tasks are better suited for training than others, but in the case of welding, the worker can simulate welding with the welding helmet 60 removed and the display 41 in a position allowing the worker to train himself or herself to perform the task with maximum efficiency and minimized energy during the full range of motions required in the task. Further, the LCD display can be placed in the view field of the welder's helmet to feedback to the welder the muscle loading features of their work style to facilitate training for optimal efficiency and minimized effort. This muscle training function of the apparatus in the present invention further enhances the results achieved in reducing muscle fatigue through optimization of the overall workstation design and its customization to the individual worker.

What is claimed is:

1. A method of designing a workstation having an operator interface assembly for performing a task on a workpiece comprising the steps of:

determining a plurality of muscle loading profiles for a muscle of a worker using an electrophysiological monitoring apparatus while the worker is performing a said task at a said workstation using said operator interface assembly for a plurality of different physical geometries of said operator interface assembly; and selecting a worker and workstation relative position physical geometry of the operator interface assembly for extended use by the worker based upon the one of said plurality of different physical geometries of said operator interface assembly producing a most desirable muscle loading profile for the worker during said determining step.

2. The method as defined in claim 1 wherein, said operator interface assembly is a fixture assembly; and said determining step is accomplished by varying the physical geometry of said fixture assembly.

3. The method as defined in claim 1 wherein, said determining step is accomplished by attaching a plurality of electrodes of a surface electromyography apparatus to monitor muscle activity of the worker when performing the task at said workstation, monitoring micro-voltages generated by at least one muscle of the worker during performance of said task to generate said plurality of muscle loading profiles, altering the physical geometry of said operator interface assembly to change the worker and operator interface assembly relative position, and repeating said monitoring and said altering steps to produce said plurality of muscle loading profiles using said surface electromyography apparatus for use of said profiles during said selecting step.

4. The method as defined in claim 3 wherein, said attaching step is accomplished by securing a plurality of micro-voltage sensing electrodes to monitor muscle loading of a plurality of muscles of said worker to simultaneously generate a plurality of muscle loading profiles.

5. The method as defined in claim 4 wherein, said selecting step is accomplished by selecting the muscle loading profile having substantially the highest muscle loading from the simultaneously sensed muscle loading profiles, and thereafter varying the physical geometry of said operator interface assembly and selecting a position of said operator interface assembly producing a reduced muscle loading profile for the selected one of the muscle loading profiles.

6. The method as defined in claim 1, and prior to said determining step, the step of:

selecting a plurality of test workers of varied representative statures typical of production workers who are to use said operator interface assembly at said workstation to perform said task.

7. The method as defined in claim 1 wherein, the determining step is accomplished at a test workstation, and after said selecting step, constructing a production workstation to have a physical geometry for said operator interface assembly substantially replicating the relative position of said worker and said test workstation to produce substantially the most desirable muscle loading profile for a worker performing said task at said production work station.

8. The method as defined in claim 7, and prior to said determining step, the step of:

employing a plurality of test workers representative of the range of likely statures of potential workers to perform said task with said operator interface assembly at said test workstation.

9. The method as defined in claim 1, and the step of:

after said selecting step, training said worker to perform said task using said operator interface assembly at said workstation while also using electrophysiological monitoring apparatus to reduce said muscle loading profile.

10. A method of designing a production workstation including an operator interface assembly for use by a production worker to perform a repetitive task comprising the steps of:

determining a plurality of muscle loading profiles for at least one muscle of a test worker while performing said task at a test workstation having an operator interface assembly with an adjustable physical geometry using a surface electromyographic apparatus;

varying the physical geometry of said operator interface assembly through a plurality of different geometries;

performing said determining step for a plurality of said varying steps;

comparing muscle loading profiles for the worker for a plurality of said varying steps;

selecting a physical geometry of the operator interface assembly producing substantially a lowest one of: (i) the average muscle loading profile, and (ii) the peak muscle load, for the test worker, as determined by said comparing step; and constructing a production workstation having an operator interface assembly employing the selected physical geometry for said operator interface assembly.

11. An apparatus for designing a workstation for use in performing a task comprising:

at least one pair of surface electromyography electrodes formed for attachment to a worker for sensing muscle loading of a muscle of the worker, said electrodes being responsive to micro- voltages produced by the worker's muscles during loading to produce an output signal;

a signal processor electrically connected to said electrodes and formed to process output signals from said electrodes to produce a muscle loading profile during performance of said task by said worker; and a workstation having an operator interface assembly with an adjustable physical geometry capable of variation of the manner of movement of the worker's muscles during performance of said task.

12. The apparatus as defined in claim 11 wherein, said signal processor includes a storage device and a display device, and said storage device is formed for storing of a plurality of muscle loading profiles therein, and said display device is formed for display of at least one muscle loading profile thereon.

13. The apparatus as defined in claim 12 wherein, said signal processor includes a signal processing program stored therein formed to compare a plurality of muscle loading profiles stored in said storage device and to select a muscle loading profile having one of: (i) a lowest average muscle loading, and (ii) a lowest peak muscle loading.

14. The apparatus as defined in claim 12 wherein, said signal processor is formed for simultaneous display of a plurality of muscle loading profiles on said display device for visual selection of a most desirable muscle loading profile.

15. The apparatus as defined in claim 11 wherein, said workstation includes an adjustable physical geometry formed to enable variation of the workstation to accommodate workers of differing stature who use said workstation to perform said task.

16. A method of designing a workstation comprising the steps of:

determining a plurality of muscle loading profiles for a muscle of a worker using an electrophysiological monitoring apparatus while the worker is performing a task at a test workstation for a plurality of different worker and workstation relative positions;

selecting a worker and test workstation relative position for extended use by the worker based upon the one of said plurality of relative positions producing a most desirable muscle loading profile for the worker during said determining step;

after said selected step, constructing a production workstation to have a physical geometry substantially replicating the relative position of said worker and said test workstation to produce substantially the most desirable muscle loading profile for a worker performing said task at said production work station; and after the step of constructing a production workstation, customizing said physical geometry of said production workstation using electrophysiological monitoring apparatus for a specific production worker who is to use said production workstation.

17. The method as defined in claim 16 wherein, said customizing step is accomplished by securing a plurality of electrical muscle load electrodes to monitor muscle activity of at least one muscle of said specific production worker when positioned at said production workstation, monitoring said muscle load electrodes during performance of said task by said production worker, and further altering said physical geometry of said production workstation to determine if a reduced muscle loading profile can be achieved using a production workstation having physical geometry and relative position customized to the specific production worker.

18. A method of designing a workstation comprising the steps of:

determining a plurality of muscle loading profiles for a muscle of a worker using an electrophysiological monitoring apparatus while the worker is performing a task at a test workstation for a plurality of different worker and workstation relative positions, and during said determining step, identifying at least one portion of said physical geometry of said test workstation producing significant muscle loading profile variation as said physical geometry of said test workstation is altered;

selecting a worker and test workstation relative position for extended use by the worker based upon the one of said plurality of relative positions producing a most desirable muscle loading profile for the worker during said determining step;

after said selecting step, constructing a production workstation to have a physical geometry substantially replicating the relative position of said worker and said test workstation to produce substantially the most desirable muscle loading profile for a worker performing said task at said production workstation, and during said construction step, providing an adjustable portion on said production workstation for a physical geometry determined at said test workstation to produce significant muscle loading profile variation during said identifying step; and customizing said production workstation to a specific production worker by using electrophysiological monitoring apparatus, and wherein said customizing step is accomplished by adjusting said adjustable portion on said production workstation while said specific production worker performs said task at said production workstation.

19. The method as defined in claim 18, and the step of:

after said selecting step, reducing muscle loading on said worker using said electrophysiological monitoring apparatus while said specific production worker performs said task at said production workstation while varying said specific production worker's method of performing said task.

20. A method of designing a production workstation for use by a production worker to perform a repetitive task comprising the steps of:

determining a plurality of muscle loading profiles for at least one muscle of a test worker while performing said task at a test workstation having an adjustable physical geometry using a surface electromyographic apparatus;

varying the physical geometry of said test workstation through a plurality of different geometries;

performing said determining step for a plurality of said varying steps;

comparing muscle loading profiles for the worker for a plurality of said varying steps;

selecting a physical geometry producing substantially a lowest one of: (i) the average muscle loading profile, and (ii) the peak muscle load, for the test worker, as determined by said comparing step;

constructing a production workstation using the selected physical geometry for said test workstation; and after said constructing step, using a specific production worker who is to use said production workstation to customize the design of said production workstation by employing a surface electromyography apparatus to sense production worker muscle loading during performance of said task at said production workstation and during further variation of said production workstation physical geometry.

21. The method as defined in claim 20 wherein, said constructing step is accomplished by constructing a plurality of substantially identical production workstations, and the step of:

customizing each of said plurality of workstations for a plurality of specific production workers using surface electromyography apparatus to minimize muscle loading on each said specific production worker during performance of said task.

22. The method as defined in claim 21, and the step of:

training each of said plurality of specific production workers to perform said task at each customized production workstation using surface electromyography apparatus to sense muscle loading.

23. The method as defined in claim 22 wherein, said training step is accomplished by displaying muscle loading output signals from an electrical muscle load sensor attached to said specific production worker on a display device, and allowing said specific, production worker to view the displayed signals while performing said task to enable variation of the performance of said task to reduce muscle loading.

24. The method as defined in claim 20, and the step of:

comparing specific production worker muscle loading profiles against a predetermined muscle loading profile to determine whether muscle loading is above an acceptable level for said task.

* * * * *

UNITED STATES PATENT AND TRADEMARK OFFICE
CERTIFICATE OF CORRECTION

PATENT NO. : 6,647,288 B2
DATED : November 11, 2003
INVENTOR(S) : Peter V. Madill and Ray T. Flugger It is certified that error appears in the above-identified patent and that said Letters Patent is hereby corrected as shown below:

Column 10,
Line 21, after "optimized" and before "profiles" insert:

-- and customized workstation without undue muscle loading. This result, for example, can be due to unusual individual skeletal or muscular problems. Thus, when a worker is placed at "bioergonomically" designed production workstation 21p for customization, if the workstation cannot be customized to bring the individual production worker's muscle loading profile into an acceptable average range, the employer can use the present process as a screening technique so as not to put a square peg into a round hole. The same worker may be well suited for a different production task at a different optimized and customized workstation, but the welding of mufflers seams might cause undue muscle stress and fatigue, regardless of the adjustments made to the electromyographically designed workstation configuration. This screening saves both the worker and the employer from finding out on the job that injuries will result if the worker is placed in the position of having to perform the task.
The surface electromyography apparatus employed in the method and apparatus of the present invention is generally well known in the art. Muscle load electrodes suitable for use in the present invention can be readily obtained from a number of vendors. The muscle micro-voltage signal processor preferably takes the form of the DSP 330 Model manufactured by J&J Engineering located in Poulsborough, Washington State. The proprietary software written for this device which permits translation of the micro-voltage signals into a visual graphical display on any PC and DOS and Windows 98 operating systems and the appropriate ports can likewise be obtained from J&J Engineering. As part of the customization process, the worker's muscle loading--.

UNITED STATES PATENT AND TRADEMARK OFFICE
CERTIFICATE OF CORRECTION

PATENT NO.   : 6,647,288 B2
DATED        : November 11, 2003
INVENTOR(S)  : Peter V. Madill and Ray T. Flugger It is certified that error appears in the above-identified patent and that said Letters Patent is hereby corrected as shown below:

<u>Column 10 (cont'd),</u>
Line 60, after "performing", delete "a".
Line 61, after "task at", delete "a".

Signed and Sealed this

Thirteenth Day of April, 2004

JON W. DUDAS
*Acting Director of the United States Patent and Trademark Office*